United States Patent [19]

Rakoutz

[11] 4,250,333
[45] Feb. 10, 1981

[54] PROCESS FOR THE SELECTIVE MONOETHERIFICATION OF PYROCATECHOL

[75] Inventor: Michel Rakoutz, Oullins, France

[73] Assignee: Philagro, Lyons, France

[21] Appl. No.: 951,278

[22] Filed: Oct. 12, 1978

[30] Foreign Application Priority Data

Oct. 20, 1977 [FR] France ................................ 77 32340

[51] Int. Cl.³ ............................................ C07C 41/01
[52] U.S. Cl. .................................................. 568/652
[58] Field of Search ....................................... 568/652

[56] References Cited

U.S. PATENT DOCUMENTS 3,927,118  12/1975  Ozretich .............................. 568/652

OTHER PUBLICATIONS

Laskino et al., Chemical Abstracts, vol. 61, (1964), 11919.
Adams et al., Organic Reactions, vol. II, (1962), pp. 22-23.

Primary Examiner—Bernard Helfin
Attorney, Agent, or Firm—Browdy and Neimark

[57] ABSTRACT

Process for the selective monoetherification of pyrocatechol.

The process relates to the selective monoetherification of pyrocatechol by means of methallyl chloride.

It consists of carrying out the etherification in an aprotic solvent medium in the presence of an alkali metal carbonate or bicarbonate.

The process can be used industrially for the preparation of o-methallyloxyhenol.

9 Claims, No Drawings

PROCESS FOR THE SELECTIVE MONOETHERIFICATION OF PYROCATECHOL

The new invention relates to a process for the preparation of o-methallyloxyphenol by selective monoetherification of pyrocatechol by means of methallyl chloride.

o-Methallyloxyphenol is a compound which is in itself known and which can be used as a starting material for the synthesis of various chemical compounds and in particular for the synthesis of 2,3-dihydro-2,2-dimethyl-benzofuran-7-yl methylcarbamate, known by the name of Carbofuran, which exhibits valuable insecticidal properties.

The etherification of monohydroxybenzenes such as monophenols does not exhibit any special difficulties and can be carried out in accordance with various reactions which are in themselves known, such as, for example:

The reaction of organic halides with alkali metal phenolates,

The reaction of organic sulphates, for example alkyl sulphates, with alkali metal phenolates, The reaction of ethylenic compounds with phenols, in the presence of sulphuric acid, and The reaction of diazonium salts with phenols.

In the case of dihydroxybenzenes such as pyrocatechol, the selective monoetherification of one of the hydroxyl groups present on the benzene nucleus presents serious difficulties because each of these two hydroxyl groups can react with the etherifying agent. Hence substantial amounts of the diether are in general obtained in addition to the monoether which it is desired to obtain. Furthermore, if the etherifying agent is an allyl, propargyl or benzyl halide, the allyl, propargyl or benzyl radical frequently becomes attached to the benzene nucleus of the dihydroxybenzene starting material, with formation of nulcear-alkylation products of this dihydroxybenzene.

The formation of diethers and of derivatives resulting from the alkylation of the benzene nucleus correspondingly reduces the yield of monoether and leads to a mixture of compounds which is expensive and delicate to separate. A solution of this problem has been proposed in French Patent Application No. 2,255,279, which claims a process for the selective monoetherification of dihydroxybenzenes by means of organic halides, according to which the etherification is carried out in the presence of an alkaline earth metal hydroxide or oxide in a reaction medium consisting of a dipolar neutral solvent possessing a sulphoxide, sulphone or amide group, such as dimethylsulphoxide, dimethylacetamide, dimethylbenzamide and N-methyl-2-pyrrolidone. This process, which, according to the examples described in this French Patent Application, more particularly relates to the preparation of o-methallyloxyphenol, makes it possible to achieve satisfactory selective monoetherification with a molar ratio of monoether/diether formed which is at least 5 and in certain cases greater than 10, and at the same time restricts the percentage of alkylation products to an acceptable level.

However, this process suffers from the disadvantage that it only allows very incomplete conversion of the pyrocatechol starting material. In fact, if reference is made to the various examples which illustrate this Patent Application, it will be seen that the selective monoetherification is generally carried out using at most 0.5 mol of methallyl chloride per mol of pyrocatechol starting material, whilst the amount theoretically necessary to achieve conversion of the whole of the pyrocatechol starting material to o-methallyloxyphenol is 1 mol of methallyl chloride per mol of pyrocatechol.

Thus, Example 1 of this French Patent Application describes the use of 0.48 mol of methallyl chloride per mol of pyrocatechol and Examples 3 to 11 describe the use of 0.5 mol of methallyl chloride per mol of pyrocatechol starting material. Example 2 shows that according to this process the use of larger amounts of methallyl chloride results in the formation of substantial amounts of diether, and in this case the monoether/diether ratio is much less than 5.

The fact that an amount of methallyl chloride equal to half the amount theoretically necessary is used of course restricts the formation of diether to an acceptable level but on the other hand results in very incomplete conversion of the pyrocatechol starting material, with a degree of conversion necessarily less than 50%, due to the formation of the diether, and in the practice of the order of 40%. Under these conditions, the yield of monoether relative to pyrocatechol starting material is thus itself necessarily very much less than 50% and in practice less than 40%. Thus, according to the conditions indicated in Example 1 of the said Patent Application, this yield is 34%. This low yield of monoether relative to the pyrocatechol starting material correspondingly reduces the industrial profitability of the process. Furthermore, the reaction mixture resulting from this process contains large amounts of unreacted pyrocatechol, which is an expensive product. The extraction of the monoether from this reaction mixture, and the recovery of the unreacted pyrocatechol for recycling require delicate and expensive separation processes. Another disadvantage of the process claimed in this French Patent Application is that it requires the use of alkaline earth metal hydroxides or oxides such as baryta, which are generally fairly expensive for industrial use. Finally, this process imposes very strict conditions in respect to the choice of the solvent which can be used industrially.

The process according to the present invention proposes to overcome these disadvantages. It makes it possible to carry out the selective monoetherification of pyrocatechol with, at one and the same time, a molar ratio of monoether/diether formed which is greater than 5 and in certain cases greater than 10 and a yield of monoether, relative to the pyrocatechol starting material, greater than 40% and in certain cases greater than 70%, whilst at the same time restricting the formation of benzene nucleus alkylation products to an acceptable level.

The process according to the invention consists of etherifying pyrocatechol by means of methallyl chloride, the said process being characterised in that the reaction is carried out in an aprotic solvent medium in the presence of an alkali metal carbonate or alkali metal bicarbonate.

According to the invention, the amount of methallyl chloride used must be such that the molar ratio of methallyl chloride/pyrocatechol starting material is between 0.6 and 2 and preferably between 1 and 1.5.

The carbonates or bicarbonates which can be used according to the invention correspond respectively to the formulae $Me_2CO_3$ and $MeHCO_3$, in which Me represents an alkali metal atom, preferably a sodium atom or potassium atom.

According to the invention, the amount of carbonate or bicarbonate to be used must be such that the ratio of the number of gram atoms of alkali metal to the number of mols of pyrocatechol starting material is between 0.5 and 2 and preferably between 0.6 and 1.2 which is the case of the bicarbonate MeHCO$_3$ corresponds to a molar ratio MeHCO$_3$/pyrocatechol starting material of between 0.5 and 2 and preferably between 0.6 and 1.2 and in the case of the carbonate Me$_2$CO$_3$ corresponds to a molar ratio Me$_2$CO$_3$/pyrocatechol starting material of between 0.25 and 1 and preferably between 0.3 and 0.6.

The aprotic solvents which can be used according to the invention can be selected from amongst the following groups: amides, such as dimethylformamide, dimethylacetamide and N-methylpyrrolidone, nitriles, such as acetonitrile, sulphoxides, such as dimethylsulphoxide, ethers, such as dioxane, tetrahydrofurane and diglyme (the dimethyl ether of diethylene glycol), aromatic hydrocarbons such as benzene, the xylenes, toluene and ethylbenzene, and aliphatic hydrocarbons, such as n-octane.

In practice, the use of N-methylpyrrolidone as a solvent gives good results. According to the invention, the aprotic solvent medium can consist either of a single aprotic solvent or of a mixture of aprotic solvents. Thus, for example, the use, as a solvent medium, of a mixture which comprises, by weight, 90% of n-octane 10% of N-methylpyrrolidone, gives good results.

The reaction temperature, pressure and time are not critical. In practice, the process is carried out under atmospheric pressure at a temperature of between 50° C. and 140° C. for a period which can vary approximately from 1 hour to 20 hours.

The separation and isolation of the monoether from the reaction medium can be effected by known means such as distillation or extraction.

The examples which follow are given in order to illustrate the invention, without however implying a limitation.

EXAMPLE 1

150 ml of N-methylpyrrolidone, 11 g of pyrocatechol (representing 0.10 mol) and 7 g of potassium carbonate (representing 0.05 mol) are introduced into a 250 ml three-necked flask purged with nitrogen and equipped with a central stirrer, a reflux condenser and a dropping funnel. The above mixture is heated to 90° C., whilst stirring, and 13.6 g (15 ml, representing 0.15 mol) of methallyl chloride are run in over 3 hours at the rate of 5 ml per hour. When this addition has ended, the mixture is stirred for a further 1 hour 35 minutes at 90° C. A chromatographic determination carried out at that stage shows that there still remain 4.9 g of unreacted methallyl chloride. The experiment is now stopped, the reaction mixture is cooled, 250 ml of distilled water are added and the batch is neutralised to pH 7 by adding 50% strength sulphuric acid. This aqueous-organic mixture is extracted with 6 × 80 ml of ethyl acetate. Argentimetry on the residual aqueous phase shows the presence of $8.7 \times 10^{-2}$ gram ions of Cl$^-$. The ethyl acetate extract is found to contain 2.2 grams of unconverted pyrocatechol (representing 0.020 mol), 11.2 grams of o-methallyloxyphenol (representing 0.068 mol) and 2 grams of o-dimethallyloxybenzene (representing 0.009 mol), corresponding to the following results:

Percentage of pyrocatechol converted: 80%.

Yields relative to pyrocatechol converted: o-methallyloxyphenol, 85%; o-dimethallyloxybenzene, 11%

Yield of o-methallyloxyphenol relative to pyrocatechol

Starting material: 68%

Molar ratio of o-methallyloxyphenol/o-dimethallyloxybenzene: 7.6.

The amount of benzene ring alkylation products formed was not determined directly. In the examples described, the yield of these products relative to pyrocatechol converted can however be evaluated from the yields of monoether and diether relative to the pyrocatechol converted. In the present example, this yield is about 4%.

EXAMPLES 2 TO 11

For these examples, the method described in the preceding example is followed, using N-methylpyrrolidone as the solvent. The conditions used as well as the results obtained are indicated in the table below, in which the entries shown on the first line have the following meaning:

CM/PY start: molar ratio of the amount of methallyl chloride used to the amount of pyrocatechol starting material.

Me/PY start: ratio of the number of gram atoms of alkali metal of the alkaline reagent used to the number of mols of pyrocatechol starting material.

% PY conv.: percentage of pyrocatechol converted relative to the pyrocatechol starting material.

Yield mono/PY conv.: yield (in %) of o-methallyloxyphenol relative to the pyrocatechol converted.

Yield di/PY conv.: yield (in %) of o-dimethallyloxybenzene relative to the pyrocatechol converted.

Mono/di: molar ratio of o-methallyloxyphenol/o-dimethallyloxybenzene formed.

Yield mono/PY start: yield (in %) of o-methallyloxyphenol relative to the pyrocatechol starting material.

| Example No. | Alkaline reagent | CM/PY start | Me/PY start | Temperature °C. | Duration | % PY conv. | Yield mono/PY conv. % | Yield di/PY conv. % | Mono/di | Yield mono/PY start % |
|---|---|---|---|---|---|---|---|---|---|---|
| 2 | NaHCO$_3$ | 0.67 | 0.67 | 130° | 2hrs.30 | 59 | 83 | 5 | 16 | 49 |
| 3 | Na$_2$CO$_3$ | 1.15 | 1.57 | 130° | 3hrs. | 93 | 79 | 15 | 5.5 | 73 |
| 4 | Na$_2$CO$_3$ | 1.1 | 1.5 | 130° | 1hr.10 | 93 | 79 | 15 | 5.5 | 73 |
| 5 | Na$_2$CO$_3$ | 1 | 1 | 130° | 1hr.50 | 83 | 83 | 11 | 7.5 | 69 |
| 6 | K$_2$CO$_3$ | 1.1 | 1 | 60° | 16hrs. | 89 | 75 | 15 | 5 | 67 |
| 7 | K$_2$CO$_3$ | 1.1 | 1 | 90° | 6hrs. | 76 | 80 | 14 | 5.7 | 61 |
| 8 | K$_2$CO$_3$ | 0.73 | 0.67 | 92° | 2hrs.10 | 59 | 79 | 8 | 9.9 | 47 |
| 9 | K$_2$CO$_3$ | 1.1 | 1 | 90° | 3hrs.15 | 76 | 78 | 12 | 6.5 | 59 |
| 10 | K$_2$CO$_3$ | 1 | 1 | 130° | 1hr. | 91 | 80 | 9 | 8.9 | 73 |

EXAMPLE 11

The apparatus described in Example 1 is used and is charged with 60 ml of dimethylsulphoxide, 11 g of pyrocatechol (representing 0.1 mol) and 7 g of potassium carbonate $K_2CO_3$ (representing 0.1 gram atom of K).

The stirred mixture is heated to 90° C., whilst stirring. 12 ml (11 g, representing 0.11 mol) of methallyl chloride are then run in, divided into portions of 3 ml every quarter of an hour.

When all has been run in, heating is continued for 3 hours 30 minutes and the mixture is then treated as indicated in Example 1. $9.3 \times 10^{-2}$ gram ion of $Cl^-$ are found in the extracted aqueous phase, whilst the organic phase is found to contain 2.2 g, representing 0.02 mol, of unconverted pyrocatechol, 10 g, representing 0.061 mol, of o-methallyloxyphenol and 2.7 g, representing 0.0123 mol, of o-dimethallyloxybenzene, which corresponds to the following results:

% of pyrocatechol converted: 80%.
Yield relative to pyrocatechol converted:
monoether 76%
diether 15%
Yield of monoether/pyrocatechol starting material: 61%
Molar ratio of monoether/diether: 5.1.

EXAMPLE 12

The procedure followed is as before, 70 ml of diglyme (dimethyl ether of diethylene glycol), 11 g of pyrocatechol (0.1 mol) and 5.5 g of $Na_2CO_3$ (0.1 gram atom of Na) being charged into the apparatus described in Example 1.

The stirred mixture is heated to 130° C. and 9.05 g (0.1 mol) of methallyl chloride are run in over 30 minutes. After 5 hours 45 minutes reaction time at this temperature, the experiment is stopped. No further methallyl chloride is detected by vapour phase chromatography. After treatment in accordance with the method described in Example 1, the following are found: 5.4 g of unconverted pyrocatechol (0.049 mol), 6.9 g of o-methallyloxyphenol (0.041 mol) and 0.6 g of o-dimethallyloxybenzene (0.0027 mol). This corresponds to the following results:

% of pyrocatechol converted: 51%.
Yield relative to pyrocatechol converted:
monoether: 82%
diether: 5%
Yield of monoether/pyrocatechol starting material: 42%.
Molar ratio of monoether/diether: 16.

EXAMPLE 13

6 ml of N-methylpyrrolidone, 50 ml of n-octane, 3.3 g of pyrocatechol (0.03 mol) and 2.1 g of $K_2CO_3$ (0.03 gram atom of K) are introduced into the apparatus described in Example 1.

The heterogeneous three-phase mixture is heated, with stirring, to 90° C. 3 g (0.03 mol) of methallyl chloride are then run in over 25 minutes. The mixture throughout consists of two liquid phases and a suspended solid phase. It is left with vigorous stirring for 4 hours 35 minutes, after which the experiment is stopped and the mixture is treated as described earlier. A determination shows that the mixture contains 1.2 g of unconverted pyrocatechol (0.011 mol), 2.3 g of o-methallyl-oxyphenol (0.014 mol) and 0.2 g of dimethallyloxybenzene (0.0009 mol), which corresponds to the following results:

% of pyrocatechol converted: 64%.
Yield relative to pyrocatechol converted:
monoether: 74%
diether: 5%
Yield of monoether/pyrocatechol starting material: 47%.
Molar ratio of monoether/diether: 14.8.

EXAMPLE 14

100 ml of acetonitrile, 6.9 g of anhydrous potassium carbonate (representing 0.1 gram atom of K), 11 g of pyrocatechol (0.1 mol) and 9.1 g of methallyl chloride (0.1 mol) are charged into a 250 ml Erlenmayer flask equipped with a magentic stirrer and a reflux condenser.

This stirred mixture is heated under reflux for 16 hours and then cooled and treated as indicated in Example 1.

0.063 gram ion of $Cl^-$ are determined in the extracted aqueous phase whilst the ethyl acetate extract is found to contain 4.4 g of unconverted pyrocatechol (0.04 mol), 8.6 g of o-methallyloxyphenol (0.052 mol) and 0.6 g of o-dimethallyloxybenzene (0.0028 mol) which corresponds to the following results:

% of pyrocatechol converted: 60%.
Yield relative to pyrocatechol converted:
monoether: 87%
diether: 5%
Yield of monoether/pyrocatechol starting material: 52%.
Molar ratio of monoether/diether: 17.4.

COMPARISON EXAMPLES A-D

The method used for these examples is that described in Example 1 of the present Patent Application, but with the alkali metal carbonates or bicarbonates replaced by alkali metal hydroxides, with either dimethylformamide (DMF) or N-methylpyrrolidone (NMP) as the solvent medium. The operating conditions, as well as the results obtained, are indicated below:

| Example | A | B | C | D |
|---|---|---|---|---|
| Alkali metal hydroxide | NaOH | NaOH | NaOH | KOH |
| Solvent | DMF | NMP | NMP | NMP |
| CM/PY start | 0.67 | 1 | 1.5 | 1 |
| MeOH/PY start | 0.67 | 1.5 | 1 | 1 |
| Temperature | 52° | 90° | 90° | 75° |
| Duration | 5hrs.35 | 1hr.20 | 1hr.20 | 4hrs. |
| % PY conv. | 41 | 73 | 82 | 83 |
| Yield mono/PY conv., % | 87 | 59 | 63 | 66 |
| Yield di/PY conv., % | 13 | 33 | 25 | 17 |
| Mono/di | 6.7 | 1.8 | 2.5 | 3.8 |
| Yield mono/PY start, % | 36 | 43 | 52 | 55 |

These Examples A–D show that if the alkaline reagent used is sodium hydroxide or potassium hydroxide, an increase in the amount of methallyl chloride used improves the degree of conversion of the pyrocatechol as well as the yield of monoether, but results in a substantial formation of diether and of benzene ring alkylation products. Thus, if reference is made to Examples B and D, the use of one mol of methallyl chloride per mol of pyrocatechol, results in monoether/diether molar ratios of, respectively, 1.8 in Example B and 3.8 in Example D. If reference is now made to Examples 1 to 14 according to the present Patent Application, it will be seen that according to the process claimed, it is possible to use large amounts of methallyl chloride without reducing the selectivity of the reaction. Thus, according to Example 1, the use of 1.5 mols of methallyl chloride per mol of pyrocatechol makes it possible to achieve a molar ratio of monoether/diether of 7.6, whilst having a yield of 68% of o-methallyloxyphenol relative to the pyrocatechol starting material, and a content of benzene nucleus alkylation products of 4% relative to pyrocatechol converted.

I claim:

1. Process for the etherification of pyrocatechol by means of methallyl chloride, characterised in that the raction is carried out in an aprotic solvent medium in the presence of an alkali metal carbonate or bicarbonate.

2. Process according to claim 1, characterised in that the amounts of pyrocatechol, methallyl chloride and alkali metal carbonate or bicarbonate used are such that the molar ratio of methallyl chloride/pyrocatechol starting material is between 0.6 and 2 and the ratio of the number of gram atoms of alkali metal to the number of mols of pyrocatechol starting material is between 0.5 and 2.

3. Process according to claim 2, characterised in that the alkali metal is sodium or potassium.

4. Process according to claim 3, characterised in that the aprotic solvent medium consists of at least one aprotic solvent selected from amongst amides, nitriles, sulphoxides, ethers, aromatic hydrocarbons and aliphatic hydrocarbons.

5. Process according to claim 4, characterised in that the molar ratio of methallyl chloride/pyrocatechol starting material is between 1 and 1.5 and the ratio of the number of gram atoms of sodium or potassium to the number of mols of pyrocatechol starting material is between 0.6 and 1.2.

6. Process according to claim 2, wherein said aprotic solvent is a nitrile, ether, aromatic hydrocarbon or aliphatic hydrocarbon.

7. Process according to claim 2, wherein said aprotic solvent is a mixture of a major portion of hydrocarbon and a minor portion of N-methylpyrrolidone.

8. A process in accordance with claim 7, wherein said aprotic solvent comprises approximately 10% of said N-methylpyrrolidone and approximately 90% of n-octane.

9. A process according to claim 2, wherein said aprotic solvent is acetonitrile.

* * * * *